United States Patent [19]

Takayanagi

[11] Patent Number: 5,290,773

[45] Date of Patent: Mar. 1, 1994

[54] SULFONYL DERIVATIVES

[76] Inventor: Takeo Takayanagi, 41 Ellsworth Ave., Yonkers, N.Y. 10705

[21] Appl. No.: 497,508

[22] Filed: Mar. 21, 1990

[51] Int. Cl.$^5$ .......................... A01N 55/02; C07F 3/06; C07F 1/08

[52] U.S. Cl. ..................... 514/184; 556/114; 556/117; 556/120; 556/135; 544/252; 544/296; 544/317; 544/318; 544/327; 544/242; 548/965; 549/429; 549/497; 560/13; 562/430

[58] Field of Search ............... 560/13; 562/430; 423/414, 415 R, 416, 417, 430; 556/120, 114, 117, 135; 514/184

[56] References Cited

U.S. PATENT DOCUMENTS 4,863,910 9/1989 Takayanagi ................. 514/150
4,956,457 9/1990 Takayanagi ................. 534/643

*Primary Examiner*—Paul J. Killos
*Assistant Examiner*—Porfirio Nazario-Gonzalez
*Attorney, Agent, or Firm*—Bierman and Muserlian

[57] ABSTRACT

A sulfonyl compound of the formula

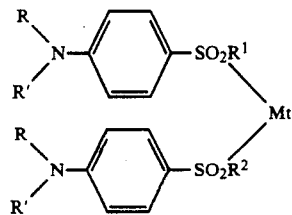

I

The above illuminated formula (I) undergo bimolecular condensation by the condensing agents and easily form simple metal salts especially metal complexes which act as combatting viruses and inhibiting tissue growth.

12 Claims, No Drawings

SULFONYL DERIVATIVES

PRIOR ART

U.S. Pat. No. 4,863,910 describes related compounds and complexes thereof.

OBJECTS OF THE INVENTION

It is an object of the invention to provide the novel salts of formula I and complexes thereof.

It is another object of the invention to provide novel compositions for inhibiting tissue growth.

These and other objects and advantages of the invention will become obvious from the following detailed description.

THE INVENTION

The novel salts of the invention are compounds of the formula

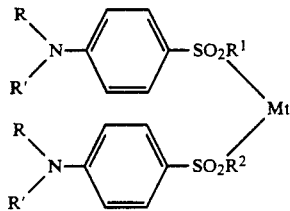

wherein R and R' are individually selected from the group consisting of hydrogen, —COCHR$_4$, —COC(R$_4$)$_3$, —SO$_2$CH$_3$, —COOCH$_2$CH$_3$, —CH$_2$—CH$_2$—R$_4$, —CH$_2$—CH$_2$OH, —CONH—CH$_2$CH$_2$R$_4$, —CONHCH$_2$COOCH$_2$CH$_3$, —CH$_2$CH$_2$OCONH$_2$, R$^4$ is Cl or a radical selected from the group consisting of

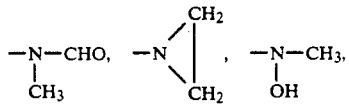

—NHCOCH$_2$CH$_2$OH, —NHCOCH$_2$CH$_3$, —NHOH, —NHCH$_3$ and —NHCONHOH, Mt is a metal, wherein

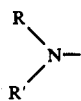

radical can be changeable to an alkyl, halogen or an aminomethyl radical. R$_1$ and R$_2$ are also selected from the group consisting of

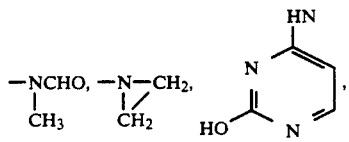

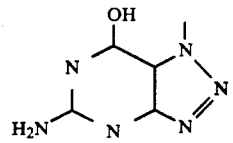

6-mercaptopurinyl, 5-fluorouracilyl, prednisolyl, salicylhydrazidyl, 1-allyl-2-thiouracilyl, hydroxylamine, isoamidyl, or R$_1$ and R$_2$ are group selected from the group consisting of —O—CH$_3$, —O—CH$_2$CH$_3$, —O—CH$_2$—OH:OH$_2$, —O—C$_6$H$_5$ or Benzhydrol or R$_1$ and R$_2$ are an ether selected from the ether group consisting of ClCH$_2$OCH$_2$C; CH$_3$OCH$_2$CH$_2$OCH$_3$ CH$_2$ClCH$_2$OCH$_2$CH$_2$Cl C$_4$H$_9$OCH$_3$ (C$_6$H$_5$)$_2$O CH$_3$—O—CHCl$_2$, (CH$_3$=CHCH$_2$)$_2$O CH$_2$=CHOCH=CH$_2$ C$_4$H$_9$OC$_4$H$_9$ C$_6$H$_5$OCH$_3$ ClCH$_2$—OC$_2$H$_5$, OHCH$_2$CH$_2$—O—CH$_2$CH$_2$Cl, ClCH$_2$CHCl—OC$_7$H$_5$

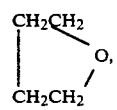

or R$^1$ and R$^2$ are an inorganic group selected from the group consisting of —(Na)SH, —(K), —(K)I, —C—Cl$_3$. Otherwise, the formula I may be condensed with an alkane sulfonyl chloride of the formula II

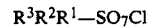    II

R$^3$R$^2$R$^1$ represent the position of the side chain.

The sulfonyl compounds of formula I undergo biomolecular condensation with alkaline condensing agents. The sulfonyl group is acidic with a strong negative charge, while the metal salts have a positive charge. At the ion exchanging time of electrophile substitution, the interspace of a pair of sulfonyl groups are seemed to be changed into the electric field and occurred attractive force in the interspace, then it has been found that several compounds were concommitantly included into the interspace of bifunctional space. In interspace were carried out various interactions on the Donor-Acceptor basis synchronously. Consequently, the formation of solid and steady hybrid compounds occurs and the ion-exchanging reaction in this invention may be illustrated in the following Fig.

In this invention, there is an excellent interspace prepared which could be admitted to several compounds at a time. In 1977, Dr. Wulf et al. (Macromol. Chem., Vol. 178, p. 2800 (1977)) described in interspace in a complex designed and have studied the inclusion effect relating bifunctional space on the Donor-Acceptor basis. Hereupon, it is to be emphasized that such a phenomenon does not occur in the monofunctional case.

The sulfonyl compounds undergo bimolocular condensation by the condensing agent and may form simple metal salts, especially pharmaceutically acceptable metal complex-salts and they are employed in the production of complex-compounds. It has been found that at the same time as the condensation (electrophilc substitution), there surprisingly occurred an inclusion phenomenon and can be condensed to form concommitantly their coordinate metal sulfonyl-complex including several compounds selected from the group consisting of antitumor-agents such as Nitrogen-mustard, cyclophosphamide thiothepa vinblastin, myleran and $CH(NHCH_2CH_2Cl)_3$.

Examples of compounds which can be condensed to form the compounds of formula I are prednisolone, 6-mercaptopurine, adenosine, cytosine, 5-fluorouracil, hydroxylamine and N-methylformamide, with antibiotics, coloramphenicol, streptmycin and penicillin, with curative organic dyestuffs such as pyocyanime, methyleneblue and acriflavin or organic compounds having effect such as 1-allyl-2-thiourea, vitamins, abscisic acid, chinonimine, salicylic acid methyl ester, phenylchloramine maleate, salicyl hydrazide, glucoside, colchitine and herb extract, with ferments such as hyaluronidase, lysozyme chloride, collagenase, asparaginase and metal fixed enzyme, with metal salts such as Mg, Cu, Hg, Zn and Pt, with hormones as androgen, androcortical-hormone and estrogens, also as chinone with structural formulae in the claim.

The condensation of the invention was carried out smoothly in a coherent polar solvent with a metal solution to obtain simple metal salts of formula I. When in the presence of a gest - component, then the inclusion compounds were concommitantly obtained. As preferred condensing agents of the invention are salts of alkali metals, alkaline earth metal or a transition element, especially a magnesium salt.

And the inclusion components are all highly soluble in water whether they are solids or liquids. The inclusion complexes have the advantage that the intended effective agents can be brought within the complexes. Liquid substance will be pulverized, active agents which have a strong odor will be deodorized, insoluble material will be easily water soluble and high stability, detoxification of medicines because of included in the macromolecule. Furthermore, it is now substantiated that this invention has the advantage of obtaining many effective substances through adequate variation and combination of the substituents and the condensation components.

Numerous new effective compounds necessary for combination thereapy against resistant virus have been found and the new complex-compounds of this invention have accurate inhibitory properties against the growth of tissue. Therefore, the complexes are available for treatments of malignant tumors or new formation as well proportional hybrids.

The related experiment have been carried out since the year 1968 and under the support of National Cancer Institute of America. The compounds of this invention are, as above mentioned, nearly non-toxic, tasteless, stimulusless and odorless and have no side effects and are especially water soluble. Therefore these hybrids are widely applicable for clinical use.

The compounds of formula I may be condensed in a polar solvent in a coexistence of inclusive components or simply with a metal salts solution to produce the novel complex of formula I and the active agents. Examples of suitable active agents are as follows.

1. Antitumor agent such as Nitroamine, cyclophosphamide, thyothepa, 6-mercaptopurin, 5-fluorouracil, prednisolone, mylerane, and $CH(NHCH_2CH_2Cl)_3$, $C_6O_2(NHCH_2CH_2Cl)_4$. and carbamates or 2-chloroethyl-derivatives.

2. Antibiotics such as chloroamphanicol, streptomycin and penicillin.

3. Curative dyestuff such as pyoktanin, methylene blue and acriflavin.

4. Ferments such as hyaluronidase, lyzozym-chloride, collagenase L-asparaginase and fixed ferment.

5. Organic compounds such as 1-allyl-2-thioharnstoff, salicyl hydracid, N-methylformamide, abacisic acid, chlorpheniramine malesate, chinonimine, methyl salicylate, ethylenimine and glucoside.

6. Metal salts such as the sulfate or hydroxide of Mg, Cu, H, Zn or Fluorine and Pt salts.

7. Nitroso compounds such as $(CH_3)_2N-NO$, $(C_2H_5)_2N-NO$,

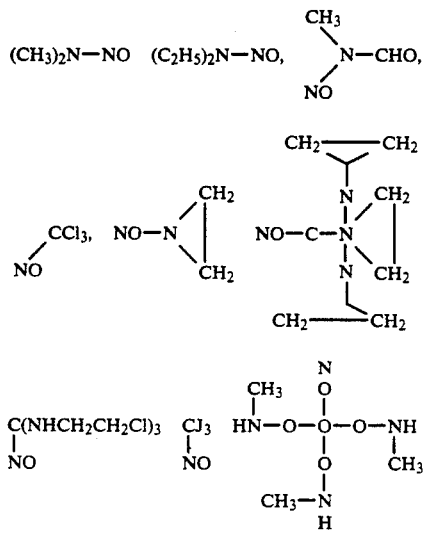

8. Hormones such as androgen, estrogen and adrenocortical hormones.

9. ethers such as

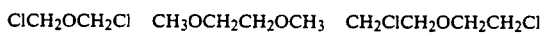

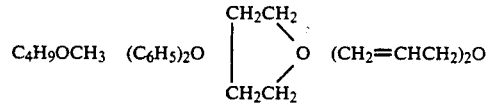

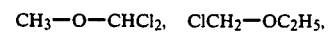

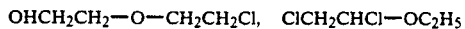

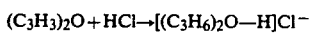

Ether forms oxonium compound with acid.

$(C_3H_3)_2O + HCl \rightarrow [(C_3H_6)_2O-H]Cl^-$ 10. o or p-quinone-groups such as
(Tetra-2(chlorethyl)amino)-o-quinone
(Tetra(N-methyl-N-formyl)amino)-o-quinone
(Tetra(N-carboethoxy)amino-o-quinone
(Tetra(N-aziridino))-o-quinone
(Tetra(N-methyl-N-hydroxyl)amino)-O-quinone.

11. Carbamic Acid Ester

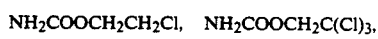

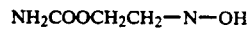

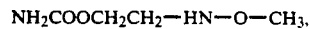

-continued

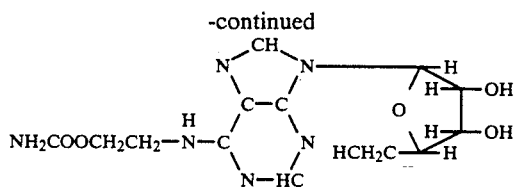

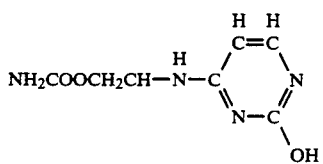

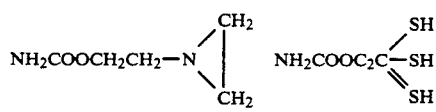

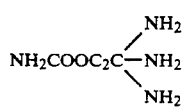

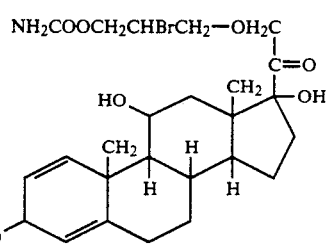

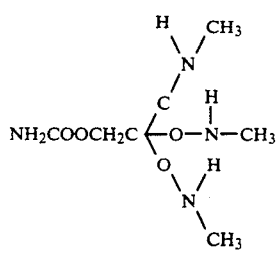

12. Chloralkyl Derivatives.

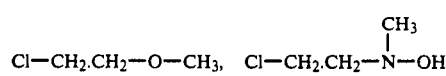

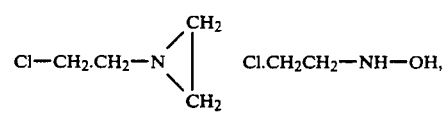

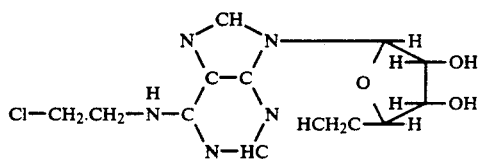

According to the invention, the preparation of the most chemotherapeutically effective sulfonyl compounds is accomplished in a solvent, particularly ethylene glycol monoethyl ether, which is characteristically coherent and causes condensation and more over dissolves the compound above mentioned.

The starting compounds of the sulfonyl compounds of formula I will be prepared in the well-known manner from p-acetamino-benzensulfonyl chloride of the formula

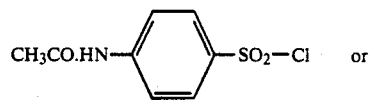

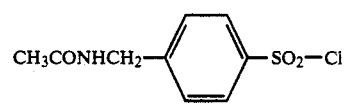

or 4-Carboethoxyamino-benzensulfonyl-chloride of the formula

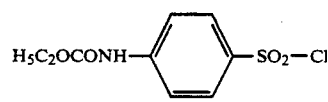

whereby the sulfonyl chloride were prepared from the substituted aromatic compounds of 5 times the amount of chlorosulfonic acid under the cooling at 10° C. Then the mixture was heated at 50° C. several hrs. And the mixture were poured into the icewater. The resulting chloride was dissolved in 30 times of pyridine and 1 mole of substituent $R^1$ was added into the solution and heated for 2 hours at 30° C. Then petroleum ether was added until the oily substance separated out. The resulting compound had the following formula

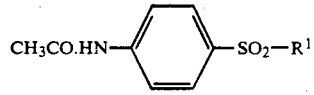

The oily product was added to 5 times of 25% HCl solution and heated for 20 minutes in a water bath to effect hydrolysis of the 4-amino radical to obtain a compound of the formula

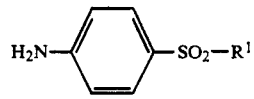

To acetylate the 4-amino group, 1 or 2 molar amounts of the acid chloride were reacted at 10° C. When one mole of dichloro or trichloroacetyl chloride were used, the compounds of the following formula were formed

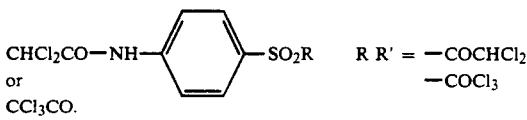

When 2 moles of acid chloride were used with heating at 160° to 180° C. and optionally a catalyst was used, there were formed compounds of the formula

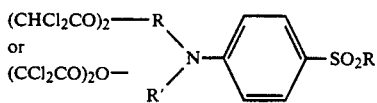

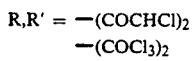

Instead of acid chlorides, the acid anhydride or isocyanate could be employed.

By reacting the 4-amino radical with an equimolar amount of 2-chlorethyl isocyanate a compound of the formula was obtained.

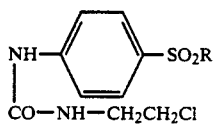

The substitution of above mentioned 4-amino radical with ethylene oxide was carried out in a dioxane solution by adding small amounts of water to obtain a compound of the formula

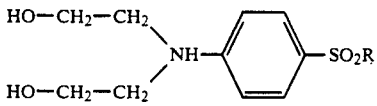

Instead of ethylene oxide, another adequate alkylene oxide can be used.

The obtained oxide substance was dissolved in 20 times of pyridine with small quantities of pyridine and while heating, 2 moles of thionyl chloride were added dropwise. The effected mass was isolated to obtain a compound of the formula

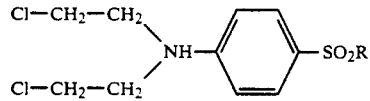

In the following examples there are described several preferred embodiments to illustrate the invention. However, it is to be understood that the invention is not intended to be limited to the specific embodiments.

EXAMPLE 1

2 g of 4-carbethoxyamino-benzene sulfonyl chloride and 1 g of 1-allyl-2-thiourea were dissolved in 30 ml of pyridine and the mixture was heated to 30° C. and stood overnight. Then, petroleum ether was poured into the mixture until an oil phase began to separate out and the oil phase was dissolved in 30 ml of 2-methoxyethanol. Predisolone carbamate, 6-mercapto-purine, 2-chloroethyl hydroxyamine and hyaluronidase were added to the mixture in a 1:1 ratio and the mixture was added to 30 to 40% by weight of magnesium sulfate solution with vigorous stirring until the solution completely coagulated. The product was washed with petroleum ether and air-dried on filter paper to obtain an easily water-soluble complex which decomposed at 180° C. and has the following formula

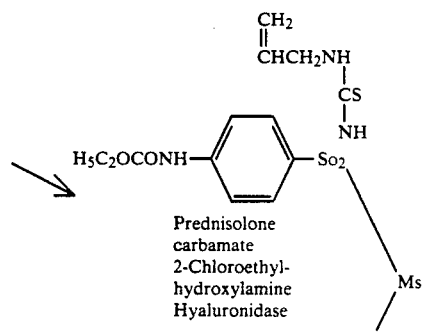

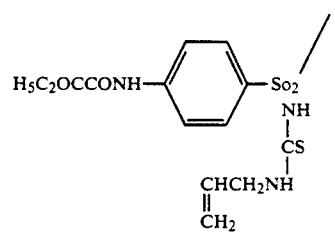

Reaction Scheme

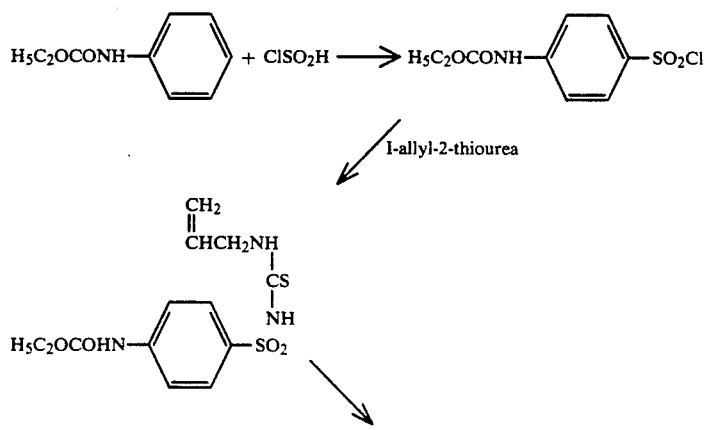

Reaction Scheme

-continued

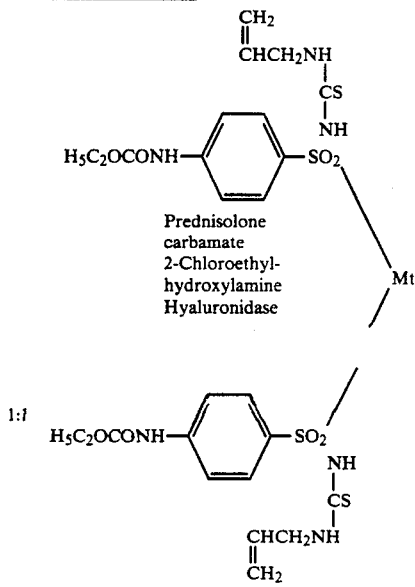

Prednisolone carbamate
2-Chloroethyl-hydroxylamine
Hyaluronidase

1:1

EXAMPLE 2

5 g of 4-carbethoxyamino-benzene sulfonyl chloride and salicyl hydrazide were dissolved in 30 ml of pyridine and the mixture was heated at 30° to 40° C. for 2 hours. The mixture stood overnight and then petroleum ether was added thereto until an oily phase separated out. The oil was dissolved in 30 ml of 2-methoxyethanol and a mixture of adenosine carbamate, 5-fluorouracil, (tetra(M-aziridine))-O-chinone and nitroso iodoform were added to the mixture in a 1:1 ratio. The mixture was added with vigorous stirring to a concentrated magnesium sulfate solution until complete coagulation occurred. The product was rinsed with petroleum ether and was dried on filter paper to obtain an extraordinarily water-soluble complex which decomposed at 180° C. and had the following formula

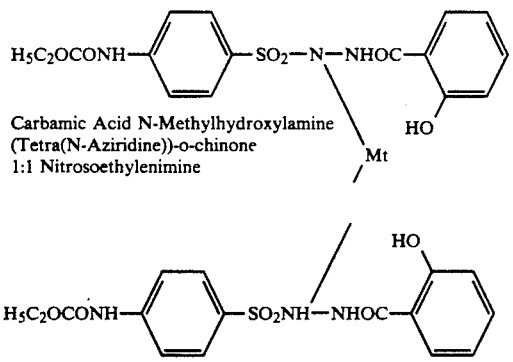

Carbamic Acid N-Methylhydroxylamine
(Tetra(N-Aziridine))-o-chinone
1:1 Nitrosoethylenimine

EXAMPLE 3

2.5 g of 4-acetamido-benzene sulfonyl chloride and 1 g of ethylurethane were dissolved in 30 ml of pyridine and the mixture was heated at 30° to 40° C. for 2 hours and stood overnight. Then petroleum ether was poured into the mixture until an oil phase separated out and the oil phase was dissolved in 30 ml of 25% hydrochloric acid. The mixture was heated on a water bath for 15 minutes to effect hydrolysis and the hydrolyzed product was isolated from the mixture.

The acetylation of the free amino group was effected by dissolving the hydrolyzed product in 30 ml of pyridine and then adding one mole of dichloroacetyl chloride with cooling. The mixture was poured into ice water and the precipitated product was isolated and dried. The product was dissolved in 30 ml of pyridine and two equivalents of ethyleneimine and the mixture was heated at 30° to 40° C. and stood overnight to obtain a viscous mass having the following formula

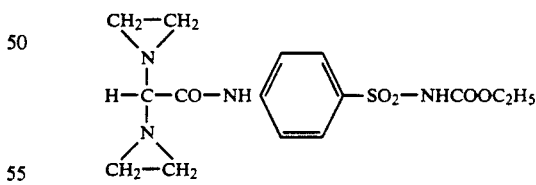

EXAMPLE 4

The viscous mass of Example 3 was dissolved in 40 ml of 2-methoxyethanol and then 2-chloroethyl methyl ether, methylformamido carbamate and $(CH_2Cl\!-\!CH_2)_3C\!-\!NO$ were added in a 1:1 ratio to the mixture. A concentrated magnesium sulfate solution was added to the mixture with stirring until complete coagulation occurred. The product was filtered and air-dried on filter paper to obtain an extradordinarily water-soluble complex decomposing at 180° C. and having the formula

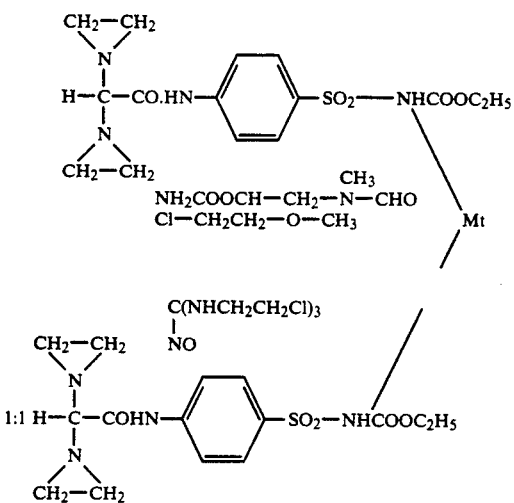

EXAMPLE 4

2.6 g of 4-carboethoxyamino-benzene sulfonyl chloride were dissolved in 40 ml of pyridine and 1.5 ml of monochloromethyl methyl ether were added dropwise with cooling. The mixture stood overnight and then petroleum ether was poured into the mixture to separate out an oil phase. The oil phase was dissolved in 40 ml of 2-methoxyethanol and then a mixture of chloroethyl carbamate, nitrosoethyleneimine and 2-chloroethyl-N-methylformamide were added in a 1:1 ratio. A concentrated magnesium sulfate solution was added dropwise to the mixture until complete coagulation occurred. The product was washed with petroleum ether and air-dried on filter paper to obtain an extraordinarily water-soluble complex decomposing at 180° C. and having the formula

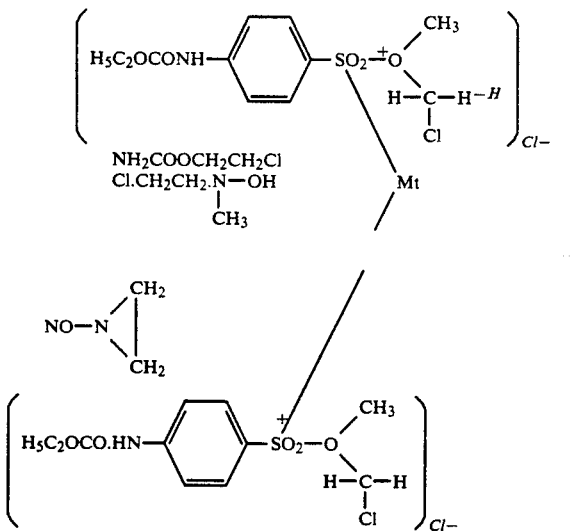

EXAMPLE 5

2.5 g of 4-carbomethoxyamino-benzene sulfonyl chloride were dissolved in 30 ml of pyridine and then 1.5 ml of bis(2-chloroethyl ether were added dropwise to the solution. The mixture stood overnight at room temperature and then petroleum ether was added thereto until an oil phase separated out. The oil phase was dissolved in 40 ml of 2-methoxyethanol and then prednisolone carbamate, nitrosohaloform and tetra (N-metyl-N-formyl-amino)-O-chinon were added thereto in a 1:1 ratio. A concentrated magnesium sulfate solution was added dropwise thereto with stirring until complete coagulation occurred. The resulting complex was highly water-soluble and decomposed at 180° C. and had the formula

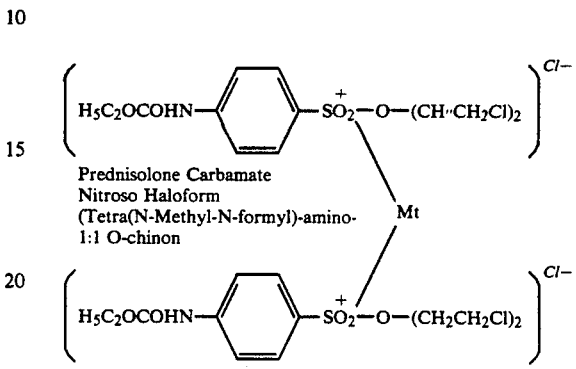

EXAMPLE 6

2.6 g of 4-carboethoxyamino-benzene sulfonyl chloride, 0.5 g of 2-chloroethyl-amine and 0.5 g of ethyl urthane dissolved in 40 ml of pyridine were heated at 30° to 40° C. for 2 hours and then stood overnight at room temperature. Petroleum ether was added to the mixture until an insoluble oil separated out and the oil was dissolved in 40 ml of 2-methoxy-ethanol. And mixture of fixed diastase, CH(NHCH$_2$CH$_2$Cl)$_3$, nitrosodiethlamine, herb extract and a 30% of cupric sulfate solution was added dropwise with stirring until the mixture was completely coagulated. The product was air-dried on filter paper to obtain an easily water-soluble condensation product melting at 180° C. and having the formula

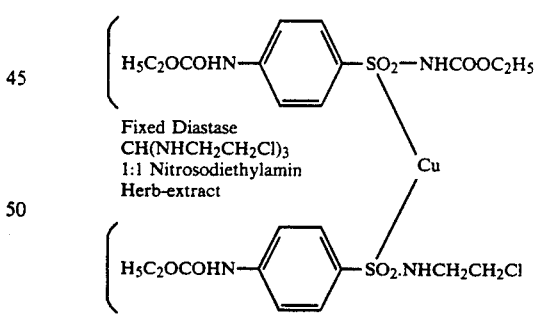

EXAMPLE 7

A mixture of 2 g of 4-carbethoxyamino-benzene sulfonyl chloride, 1 g of potassium iodide and 10 ml of distilled water was heated in a water bath at 50° C. for 2 hours and was then filtered. The product was air-dried and dissolved in 40 ml of 2-methoxyethanol. A mixture of prednisolone carbamate, Nitrosethylenimine, Lysozyme Chloride and (Tetra-(2-[2-chloroethyl)-amino]-p-chinon was added to the solution in portions in a 1:1 ratio with stirring and then a 30 to 40% magnesium sulfate solution was added dropwise until there was complete coagulation. The product was air-dried to obtain an easily water-soluble product which carbonized with decomposition at 180° C. and having the formula

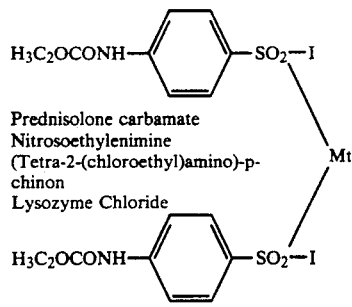

Prednisolone carbamate
Nitrosoethylenimine
(Tetra-2-(chloroethyl)amino)-p-chinon
Lysozyme Chloride

EXAMPLE 8

2 g of 4-carbethoxyamino-benzene sulfonyl chloride were dissolved in 40 ml of pyridine and 1 g of 2-Chlorethylamine were added dropwise with cooling. The solution stood overnight at room temperature and then petroleum ether was added thereto until an oil layer separated out. The oil was dissolved in 2-methoxyethanol and a prednisolone carbamate, 5-fluorouracil and (Tetra(N-Methyl-N-hydroxyl)-O-chinone was added thereto in portions. A 30 to 40% magnesium sulfate solution was added dropwise with stirring until complete coagulation occurred and the product was air-dried on filter paper. The product was easily water-soluble and carbonized with decomposition at 180° C. The product had the formula

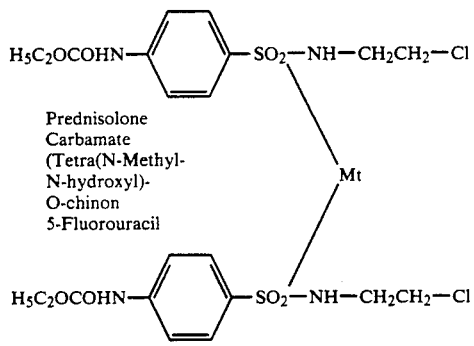

Prednisolone
Carbamate
(Tetra(N-Methyl-N-hydroxyl)-
O-chinon
5-Fluorouracil

Various modifications of the compositions and method of the invention may be made without departing from the spirit or scope thereof and it is to be understood that the invention is intended to be limited only as defined in the appended claims.

What is claimed is:

1. A complex or sulfonyl compound of the formula

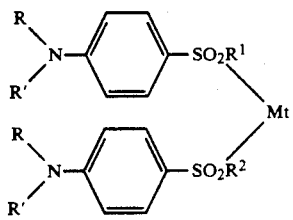

I wherein R and R' are individually selected from the group consisting of hydrogen, —COCHR$_4$, —COC(R$_4$)$_3$, —SO$_2$CH$_3$, —COOCH$_2$CH$_3$, —CH$_2$CH$_2$—R$_4$, —CH$_2$—CH$_2$OH, —CONH—CH$_2$CH$_2$R$_4$, —CONHCH$_2$COOCH$_2$CH$_3$, —CH$_2$CH$_2$OCONH$_2$, R$_4$ is a member selected from the group consisting of Cl,

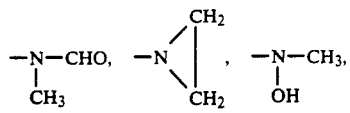

—NHCOCH$_2$CH$_2$OH, Mt is magnesium wherein

can be changeable to an alkyl, halogen or an aminomethyl, R$^1$ and R$^2$ are selected from the group consisting of

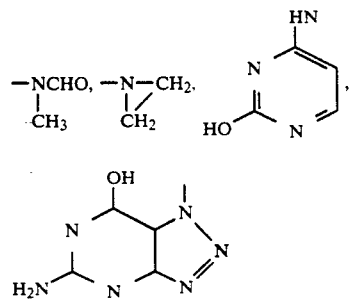

6-mercaptopurinyl, 5-fluorouracilyl, prednisolyl, salicylhydrazidyl, 1-allyl-2-thioracilyl, hydroxylamine, isamidyl or R$_1$ and R$_2$ are selected from the group consisting of —O—CH$_3$, —O—CH$_2$CH$_3$, —O—CH$_2$—CH:CH$_2$, —O—C$_6$H$_5$ or Benzhydrol, or R$^1$ and R$^2$ is an ether selected from the ether group consisting of ClCH$_2$OCH$_2$Cl    CH$_3$OCH$_2$CH$_2$OCH$_3$
CH$_2$ClCH$_2$OCH$_2$CH$_2$Cl    C$_4$H$_9$OCH$_3$    (C$_6$H$_5$)$_2$O
CH$_3$—O—CHCl$_2$,    (CH$_2$=CHCH$_2$)$_2$O
CH$_2$=CHOCH=CH$_2$    C$_4$H$_9$OC$_4$H$_9$    C$_6$H$_5$OCH$_3$
ClCH$_2$—OC$_2$H$_5$,    OHCH$_2$CH$_2$—O—CH$_2$CH$_2$Cl,
ClCH$_2$CHCl—OC$_2$H$_5$

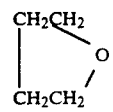

or R$^1$ and R$^2$ are an inorganic group selected from the group consisting of —(Na)SH, —(K)F, —(K)I, —C—Cl$_3$ with a condensing agent.

2. A metal complex of a compound of claim 1 including antitumor agent selected from the group consisting of nitrogen mustard, cyclophosphoamide, thyothepa, 6-mercaptopurine, 5-fluorouracil, vinblastine, L-asparaginase, carbamate and chloroethyl.

3. A metal complex of a compound of claim 1 including antibiotic selected from the group consisting of chloramphenicol and penicillin.

4. A metal complex of a compound of claim 1 including curvative organic pigment selected from the group consisting of pyoktanin (methyl violet), methylene blue and acriflavin.

5. A metal complex of a compound of claim 1 including organic compound selected from the group consisting of 1-allyl-2-thiourea, N-methylformamide, abscisis acid, quinonimine, saliylic acid methyl ester, d-maleic acid chloropheniramine, salicyl hydrazide, glucoside and cholchicine.

6. A metal complex of a compound of claim 1 including ferment selected from the group consisting of hyaluronidase, lysozyme chloride, collagenase, diastase and metal fixed ferment.

7. A metal complex of a compound of claim 1 including hormone selected from the group consisting of androgen, adrenocortical hormone and estrogen.

8. A metal complex of a compound of claim 1 including quinone compound selected from the group consisting of (Tetra-2(chlorethyl)amino-o-quinone
(Tetra(N-methyl-N-formyl)amino)-o-quinone
(Tetra(N-carboethoxy)amino)-o-quinone
(Tetra(N-aziridino))-o-quinone
(Tetra(N-methyl-N-hydroxyl)amino)-O-quinone.

9. A metal complex of a compound of claim 1 including nitroso compound selected from the group consisting of

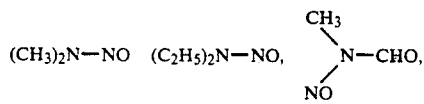

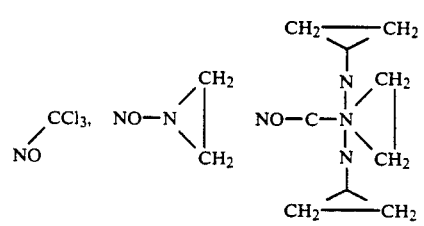

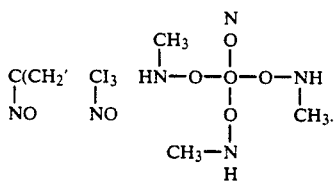

10. A metal complex of a compound of claim 1 including carbamate selected from the group consisting of

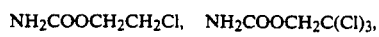

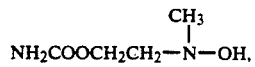

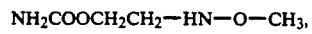

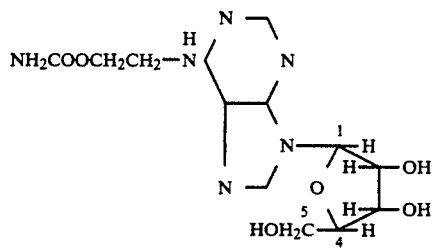

11. A metal complex of a compound of claim 1 including 2-chloro-ethyl derivative selected from the group consisting of

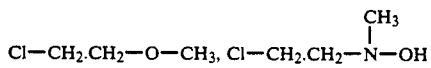

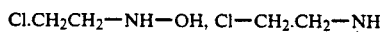

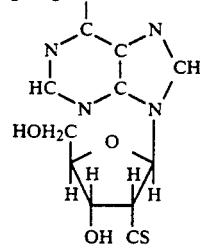

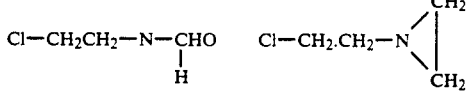

12. A composition for treating cancer comprising an amount of a complex of claim 1 sufficient to treat cancer and an inert pharmaceutical carrier.

* * * * *